United States Patent [19]

Collins

[11] 4,380,937
[45] Apr. 26, 1983

[54] SAMPLER FOR A HOT LIQUID

[76] Inventor: William J. Collins, 7005 Madison St., Merrillville, Ind. 46410

[21] Appl. No.: 253,543

[22] Filed: Apr. 13, 1981

[51] Int. Cl.³ .............................................. G01N 1/12
[52] U.S. Cl. .............................. 73/864.56; 73/864.59
[58] Field of Search ........................ 73/864.53, 864.59

[56] References Cited

U.S. PATENT DOCUMENTS

| | | | |
|---|---|---|---|
| 3,583,236 | 6/1971 | Taylor | 73/864.55 |
| 3,646,816 | 3/1972 | Hance | 73/864.58 |
| 3,994,172 | 11/1976 | Kelsey | 73/864.55 |
| 4,010,649 | 3/1977 | Falk | 73/864.55 |
| 4,069,717 | 1/1978 | Falk | 73/864.56 |
| 4,297,902 | 11/1981 | Collins | 73/864.56 |
| 4,317,380 | 3/1982 | Collins | 73/864.58 |
| 4,325,263 | 4/1982 | Gaines et al. | 73/864.55 |

*Primary Examiner*—S. Clement Swisher
*Attorney, Agent, or Firm*—Charles S. Penfold

[57] ABSTRACT

The invention or inventions are directed to devices for obtaining samples of an extremely hot liquid, such as a molten material or metal from a supply thereof for analysis.

More particularly the invention or inventions involve what may be termed sections, components or members which are so designed and constructed that they can be readily superimposed in different relationships to provide various forms of subassemblies of devices for receiving samples of an extremely hot liquid such as, for example, molten material or metal.

One of the subassemblies, for example, may include a thick section having a rear enlargement provided with a relatively large opening and a front reduced extension and a pair of appreciably thinner corresponding sections or members which have rear enlargements which cooperate with the enlargement of the thick section and the opening therein to provide a substantially enclosed chamber and frontal extensions of which at least one cooperates with the reduced extension of the thick section to provide a substantially tubular formation for supporting a tubular means for receiving some of the above mentioned material for flow into the chamber for obtaining a sample for analysis.

Another subassembly, for example, may include a pair of thick mating sections having a thin section therebetween and a pair of thin sections cooperating with the thick sections to provide a pair of chambers and a pair of substantially tubular formations for respectively supporting a pair of tubular means for receiving material for flow into the chambers to obtain samples.

38 Claims, 21 Drawing Figures

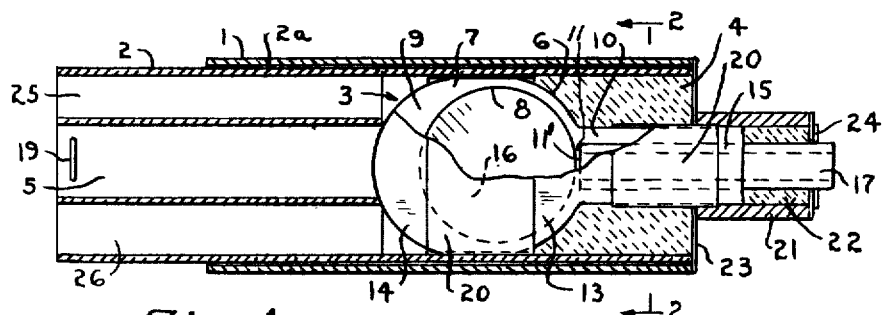
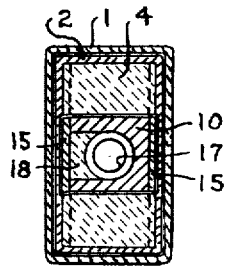
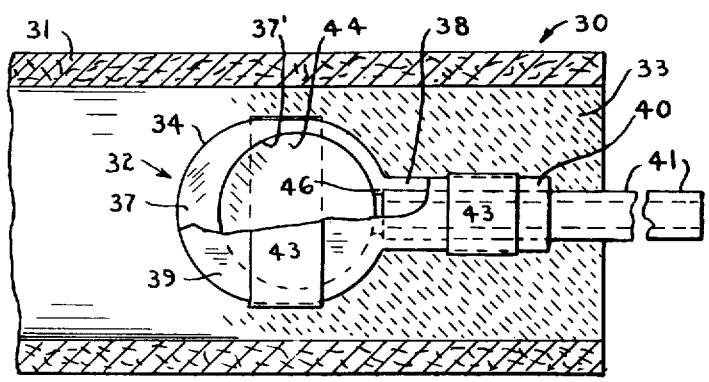
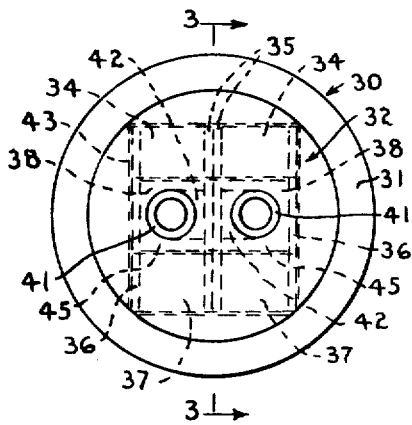
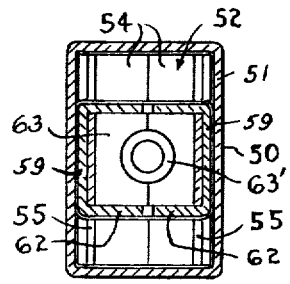
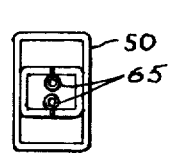
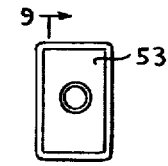
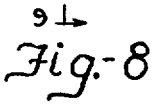
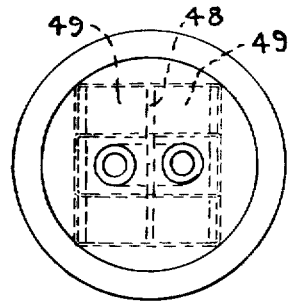
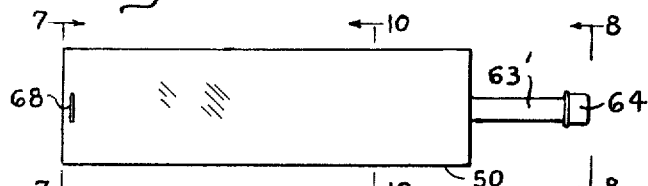
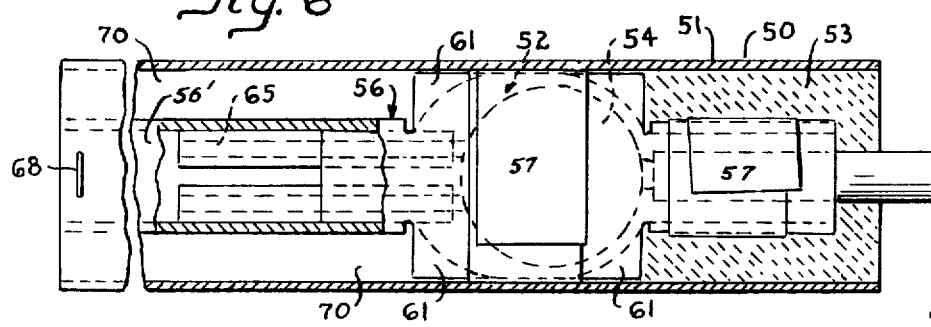

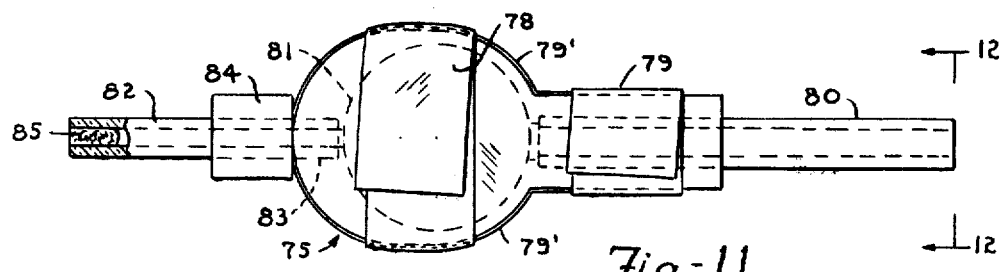
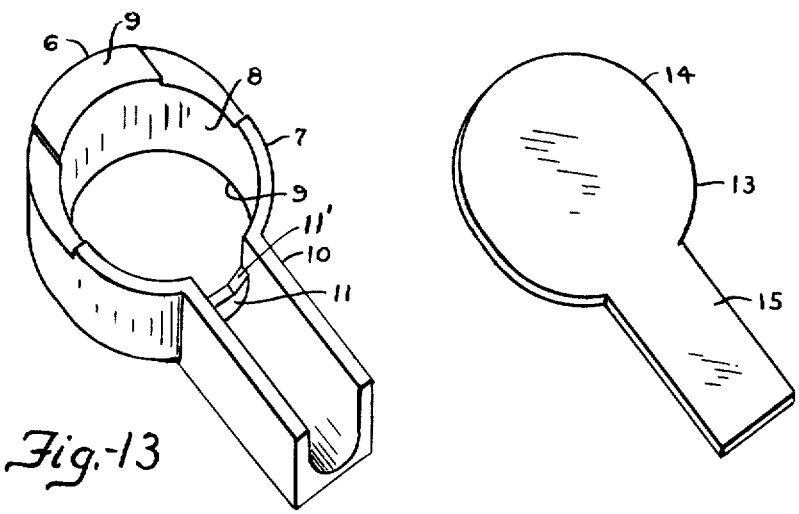
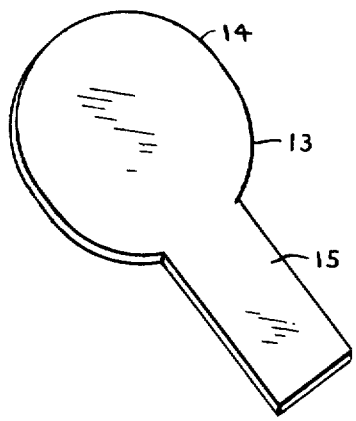
Fig.-11
Fig.-12
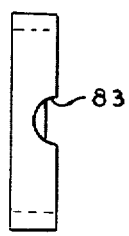
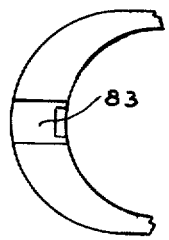
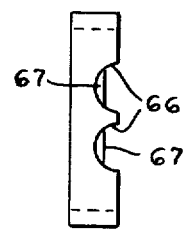
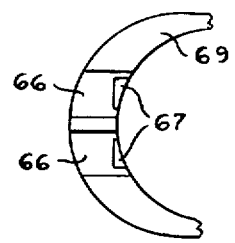
Fig.-16  Fig.-15  Fig.-18  Fig.-17
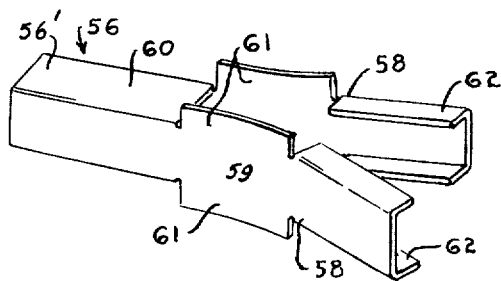
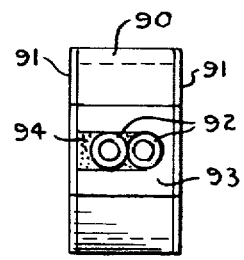
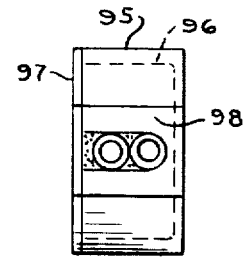
Fig.-19  Fig.-20  Fig.-21

SAMPLER FOR A HOT LIQUID

BACKGROUND OF THE INVENTION

The subject invention or inventions as alluded to above are directed to a device or devices for obtaining samples of a hot liquid, such as, for example, a molten material or metal for analysis.

Various devices for such purposes have been utilized, such as, for example, those disclosed in my U.S. Pat. Nos.: 3,552,214 dated Jan. 5, 1971; 3,656,346 dated Apr. 18, 1972 and 4,002,071 dated Jan. 11, 1977.

Reference is also made to my pending application Ser. No. 075,941 having a filing date of Sept. 17, 1979 now U.S. Pat. No. 4,297,902 and an application Ser. No. 107,157 having a filing date of Dec. 26, 1979 now U.S. Pat. No. 4,317,380.

My Patents, above referred to, disclose, among other things, a pair of thick mating sections having enlarged recessed rear extremities and front reduced channel portions which when correctly assembled provide a chamber and a tubular formation, the latter serving as a support for a tubular means for receiving a molten material for flow at the chamber for obtaining a sample from a supply of such a material.

The Patent of Edward A. Kelsey U.S. Pat. No. 3,294,172 dated Nov. 30, 1976 may be considered to be of primary interest since it discloses, among other things, a thick section having an opening and a pair of side members which engage the section to form a chamber but the thick section is not provided with any reduced front channel for accommodating a tubular means for receiving a molten material, nor does this reference, among other things, show a thin side member which cooperates with such a channel to provide a tubular formation for receiving such a tubular means.

Furthermore, all of the Patents and the disclosures in my pending application, above referred to, fail to disclose the invention or inventions disclosed and claimed in the subject application which includes the use of a plurality of sections which can be readily arranged in different superimposed relationships to provide variable forms of subassemblies of devices for obtaining samples of molten material.

OBJECTIVES OF SUBJECT INVENTION

In view of the above, an important object of the invention is to provide a device having an internal subassembly which is comprised of three sections of which one is thick and the other two are appreciably thin for cooperation with the thick section to provide a chamber and a substantially tubular formation for accommodating a tubular means for receiving a molten material from a supply thereof for flow into the chamber whereby to obtain a sample for analysis.

A specific but significant objective is to design and construct the pair of thin sections so that they are of a corresponding character in order to facilitate their interchangeability and reversible cooperation with one or more thick sections and thereby reduce costs with respect to manufacture and assembly.

Another object of the invention is to provide a subassembly somewhat similar to the one above described in which the subassembly includes a pair of substantially corresponding thick sections and three thin sections of which one is interposed between the thick sections and serves as a partition and the other two cooperate with outer surfaces of the thick sections to provide a pair of chambers and a pair of tubular formations for selectively supporting a pair of tubular means for receiving an extremely hot liquid, such as molten material from a supply thereof for flow into the chambers to obtain a pair of samples.

Also, an important object is to provide a device which includes a subassembly comprising a thick section having an enlarged rear extremity provided with a relatively large opening and a reduced front channel of a sufficient depth to accommodate a pair of tubular means and a pair of thin sections which cooperate with the enlarged rear extremity and opening therein and the channel to provide a chamber and a tubular formation which substantially encloses and supports inner extremities of the tubular means.

Ad additional object is to provide a device for obtaining a sample of molten material which comprises an outer housing, a subassembly therein having a reduced front extremity which extends forwardly of the housing and is supported by cement in the housing and by a front tubular enclosure or supporting means whereby to expedite removal of the subassembly from the housing, cement and supporting means and thereby facilitate obtaining a sample from the subassembly.

A particular object is to provide a subassembly comprising a pair of thick sections having rear enlarged extremities provided with large openings and with one or more recesses or means, the arrangement being such that when these thick sections and a pair of outer thin sections are correctly assembled the openings and thin sections will define a chamber and the recesses will cooperate to define one or a pair of cylindrical openings for accommodating one or a pair of tubular means for receiving material from the chamber whereby to obtain one or more samples in addition to the one received in the chamber.

Additional objects and advantages of the invention or inventions will become evident after the description hereafter set forth is considered in conjunction with the drawings annexed thereto.

DRAWINGS

FIG. 1 is a longitudinal section of a device for obtaining a sample of molten material, with a portion of the structure broken away to disclose details;

FIG. 2 is a transverse section taken substantially on line 2—2 of FIG. 1;

FIG. 3 is a longitudinal section taken substantially on line 3—3 of FIG. 4, illustrating a modified device;

FIG. 4 is a front end elevational view of the device shown in FIG. 3;

FIG. 5 is a modification of FIGS. 3 and 4;

FIG. 6 is a side elevational view of a modified device;

FIG. 7 is a rear end view of the device shown in FIG. 6 looking in the direction of the arrows 7—7;

FIG. 8 is a front end view of the device shown in FIG. 6 looking in the direction of the arrows 8—8;

FIG. 9 is an enlarged longitudinal section taken substantially on line 9—9 of FIG. 8;

FIG. 10 is a transverse section taken substantially on line 10—10 of FIG. 6;

FIG. 11 is a side elevational view of a device for use in a housing and constitutes a modification;

FIG. 12 is a front end view of the device shown in FIG. 11 looking in the direction of the arrows;

FIGS. 13 and 14 are perspective views of a thick and thin section which may be utilized in the subassemblies of FIGS. 1, 3, 5, 6, 11 and 20;

FIGS. 15 and 16 are partial views of each of a pair of thick sections used in the subassembly of the device shown in FIGS. 11 and 12;

FIGS. 17 and 18 are partial views of each of a pair of thick sections of the subassembly of the devices shown in FIG. 9;

FIG. 9 is a perspective view of a casing in which sections and components of a subassembly may be held;

FIG. 20 is an end view of a subassembly utilizing a thick section more or less corresponding of FIG. 13 and a pair of thin sections as shown in FIG. 14; and FIG. 21 is an end view of a subassembly similar to FIG. 20 which utilizes a thick recessed section and a single thin section, in which the depth of a groove in a channel extension of the thick section is of sufficient depth to accommodate a pair of tubular means.

DESCRIPTION

Referring first to the disclosure illustrated in FIGS. 1 and 2, numeral 1 is an outer elongated housing, constituting a protective shield preferably constructed of metal, 2 an inner casing of cellulosic material which is somewhat longer than the housing and a subassembly generally designated 3 which is preferably held in the inner casing by a front mass of cement 4 and a rear tubular formation 5.

The housing 1 and casing 2 are preferably rectangular or multisided in cross section, have parallel side walls and parallel upper and lower walls and a layer of cement 2a as may be used to secure the casing in the housing.

The subassembly 3 is preferably aligned and constructed to include a thick center section 6, as depicted in FIG. 13, having an enlarged rear extremity 7 provided with a relatively large opening 8 extending transversely therethrough which intersects substantially planar external surfaces 9 and also includes a reduced front channel extremity or extension 10. An intervening wall at the junction between the extremities serves to provide an abutment 11 and an entrance 11'. The surfaces 9 may be provided with interuptions, such as grooves or notches 9' as depicted in FIG. 13 which serve as vents when the sections of the subassembly are assembled.

The subassembly 3 also preferably includes a pair of thin corresponding planar sections 13, each having an enlarged rear extremity 14 and a reduced or narrow front portion or extremity 15 as depicted in FIGS. 1, 2 and 14. The rear enlarged extremities 14 of these thin sections engage the outer external surfaces 9 of the thick section and in combination with the opening 8 therein define a chamber 16 and the narrow portions 15 engage the channel extension 10 so that at least one of these portions in combination with this extension define a substantially tubular front formation for accommodating an inner extremity of a tubular means 17, preferably of a non-metallic material, such as Pyrex, which is at least partially held in place and against the abutment 11 by a mass of cement 18 disposed in the channel or tubular formation as illustrated in FIG. 2.

The subassembly is preferably of a size and shape that it can be readily inserted or pressed into the fore extremity of the casing and be firmly held therein by the mass of cement 4 which engages frontal portions of the enlarged rear extremity 7 and the front end of the rear tubular formation 5, the latter of which is preferably multisided in cross-section and fixedly secured in the casing 2 by any suitable means, such as by the staples 19. The tubular formation 5 is preferably secured in place prior to inserting the subassembly into the casing so that curved portions of the rear extremity of the subassembly will fit or nest in the fore end of the formation. This formation acts as a stop or abutment means for determining the innermost position of the subassembly. The thick and thin sections and tubular means 17 of the subassembly are preferably held in an assembled relation by tapes 20 wrapped about the rear and front extremities of the sections.

It should be observed that the subassembly is preferably secured in place so that a portion of a reduced fore end thereof extends a short distance forwardly of the housing and casing; that a fore extremity of the tubular means 17 extends forwardly of the front tubular formation of the subassembly; that a sleeve 21 surrounds the extended portion of the aforesaid tubular means; that cement 22 is disposed in the sleeve and about the tubular means; that a planar member 23 engages the marginal end edges of the housing and casing and also engages the cement 4 and is provided with an aperture through which the tubular means extends and that a planar member 24 engages the cement 22 is provided with an opening through which the tubular means 17 extends, all for the purpose of supporting, shielding or protecting the frontal portions of the device and subassembly during the operation of obtaining a sample of molten material. The sleeve 21 and members 23 and 24 are preferably constructed of a cellulosic material and are preferably adhesively secured in place. This unique organization also offers a setup whereby after a sample has been obtained the subassembly can be readily separated from the casing and housing end thereby facilitate breakage or separation of the components of the subassembly to obtain access to the sample.

The rear or center tubular formation 5 divides the rear extremity of the casing into a pair of parallel longitudinally extending areas 25 and 26 which are substantially rectangular in cross-section and afford a setup whereby either this tubular formation or either of the areas 25 and 26 on opposite sides thereof may detachably accommodate a lance whereby to facilitate manipulation of the device so that the tubular means 17 can be inserted into a supply of molten material to obtain a sample thereof. The center tubular formation is preferably of such a character that a cylindrical fore end of a lance can be forced into this formation to slightly expand the side walls of the latter or if desired the fore end may be generally square in cross-section for forcibly entry into the formation to provide a sufficient and safe frictional connection.

Referring to the modification of FIGS. 3 and 4, there is illustrated a device generally designated 30 which comprises an outer elongated housing 31, which is preferably in the form of a cylinder and constructed of a cellulosic material, such as pasteboard, and a subassembly generally designated 32 which is preferably fixedly secured in the front extremity of the housing by a mass of cement 33.

The subassembly 32 preferably includes a pair of substantially corresponding thick sections 34, which may be like the one shown in FIG. 13, a pair of substantially corresponding thin sections 35, like the section 13 in FIG. 14, interposed between the thick sections and a pair of thin sections 36 which engage outer surfaces of the thick sections. Each of the thick sections includes an enlarged rear extremity 37 provided with a large opening 37' extending transversely therethrough and a reduced channel extension or front extremity 38 and each of the thin sections includes an enlarged rear extremity 39 and a narrow extension 40. A tubular means 41, preferably constructed of a suitable non-metallic material such as Pyrex, has an inner extremity secured in each of the channel extensions 38 by cement 42.

When the thick and thin sections are superimposed as exemplified in FIG. 4 and held together by means such, as for example, by the tapes 43, the subassembly is inserted into the housing 31 and secured in place by the cement 33 which surrounds and engages portions of the subassembly end so that fore extremities of the pair of tubular means 41 will extend or project forwardly of the housing for eventual insertion into a mass of molten material to obtain a sample therefrom. It should be observed that the inner pair of thin sections 35 serve to provide a partition and that these thin sections, including the outer pair of thin sections 36 in combination with the thick sections form a pair of chambers 44 (one shown) and a pair of tubular formations 45, the latter of which accommodate the tubular means 41. It should also be noted that each of the thick sections includes an abutment 46 at the junction between its enlargement and channel extension and that this abutment serves to limit inward movement of a tubular means 41. Accordingly, a pair of large samples can be obtained from the chambers 44 and smaller samples from the tubular means 41 by utilizing the device 30.

The rear open extremity of the housing serves to detachably accommodate a lance whereby to facilitate manipulation of the device.

Referring to FIG. 5 there is disclosed a front end view of a modified device which substantially corresponds to the device 30, except for the fact that a single thin section 48 is interposed between a pair of thick sections 49 in lieu of the pair 35 in the device 30.

In FIGS. 6 through 10, 17 and 18 there is depicted a device 50 which preferably includes an elongated outer housing 51 preferably rectangular or multi-sided in cross-section and constructed of a suitable cellulosic material and a subassembly generally designated 52 which is preferably fixedly secured in a front extremity of the housing by a mass of cement 53.

The subassembly preferably includes a pair of thick sections 54, a pair of thin sections 55 mounted in an inner casing generally designated 56 of cellulosic material, with tapes 57 wrapped about the casing to secure the sections therein. The thick sections 54 and thin sections 55 may respectively substantially correspond to the thick and thin sections shown in FIGS. 13 and 14 and these sections are assembled in a superimposed relation and preferably secured in a casing 56 of the character shown in FIG. 19. This casing is preferably in the form of an elongated structure constructed of a cellulosic material and includes a rear tubular extremity 56' and a front extremity comprised of a pair of relatively movable portions 58. More specifically, the casing includes a pair of parallel side walls 59 and top and bottom walls 60. The top and bottom walls have been split so that each of the movable portions includes a pair of wings or lateral portions 61 and a pair of inturned portions 62. The wing portions 61 and material of the side walls therebetween serve to engage the outer surfaces of the enlarged rear extremities of the thin sections and the inturned portions 62 and material of the side walls therebetween serve to generally embrace the generally reduced channel extensions of the thick sections 54 and narrow portions of the outer thin sections 55 which in combination form a tubular formation 63 in which a tubular means or entrance tube 63' is secured for initially receiving molten material for flow into a chamber formed by the sections.

The relatively movable portions 58 of the casing facilitate manual insertion of the sections into the casing and the tapes 57 wrapped about these movable portions serve to hold the sections and casing assembled for subsequent placement into the outer housing for securement by the cement 53 and so that a fore extremity of the tubular means 63' extends forwardly of the housing 51 for use. If so desired, the tubular means 63' can be provided with a cap 64, the purpose of which is obvious.

The subassembly 52 preferably includes a pair of tubular means 65 constructed of a suitable non-metallic material, such as for example Pyrex, which have ends which are respectively secured in a pair of openings at the rear of the thick sections which are formed by a pair of parallel grooves 66 in each of these sections as shown in FIGS. 17 and 18 which cooperate or mate to form the openings. Each of the thick sections at the inner end of each of the grooves is preferably provided with an abutment or stop 67 which limits inward movement of the tubular means. The tubular means 65 are preferably disposed in the rear extremity 56' of the casing and this extremity may be secured in the housing by staples 68 or an adhesive. The tubular means may be considered to be jointly supported by the thick sections and the extremity 56'. The rear tubular means 65 serve to receive molten material from a primary chamber formed by the thick and thin sections so that at least three samples may be obtained for analysis.

The device may be of a length so that a lance can be inserted into the rear extremity 56' of the casing 56 or into either of a pair of adjacent longitudinal areas 70 for manipulating the device or, if so desired, the rear extremity of the device can be secured into a tubular fore end of a lance for manipulation.

Referring to FIGS. 11, 12, 15 and 16 there is depicted a modified device generally designated 75. This device includes a pair of thick sections 76 and a pair of thin sections 77 which are held in superimposed assembled relation by a pair of transversely disposed tapes 78 and tapes 79 and longitudinal extending tape 79', the latter of which more or less serve to seal edges or parting lines between the thick sections and thereby reduce or prevent flash or fins of molten material at the parting lines. The device 75 is preferably mounted in a housing, not shown, which is adapted for connection with a lance for manipulating the device so that a tubular means 80 can be inserted into a supply of molten material for obtaining a sample in a primary chamber 81 formed by the sections and a smaller sample can also be obtained in a rear tubular means 82 which has an inner end secured in an opening at the rear of the rear enlarged extremities of the thick sections, which opening is preferably formed by a pair of mating grooves 83, one of which is respectively provided in each of these sections as depicted in FIGS. 15 and 16.

The rear tubular means 82 is preferably protected by a relatively thick cellulosic sleeve 84 and the rear end of this means is also preferably provided with a filter 85 constructed of steel wool or equivalent means which serves to prevent outflow of molten material and thereby retain a sample in the tubular means in addition to a larger sample obtained from the primary chamber.

A modified subassembly of a device is disclosed in FIG. 20 and includes a relatively thick section 90, a pair of outer thin sections 91 and a pair of tubular means 92. The thick section is preferably designed to provide a relatively deep channel extension 93 so that it will accommodate the pair of tubular means 92, the latter of which can be secured in the extension by cement 94 in addition to one of the thin sections. If so desired, the rear enlarged extremity of the thick section may be provided with an opening which extends transversely therethrough as shown in FIG. 20 or, of so desired, a thick section 95 such as depicted in FIG. 21 may be provided with a recess 96, in which event, only a single thin outer section 97 is required. The section 95 includes a channel section 98 of a size which will accommodate a pair of tubular means as shown.

Having thus described my invention or inventions, it is obvious that various modifications or additions to those described may be made in the same without departing from the spirit of the invention and, therefore, I do not wish to be understood as limiting myself to the exact forms, constructions, arrangements, and combinations of the components herein shown and described.

I claim:

1. A section of a device for obtaining a sample of hot liquid from a supply thereof, said section comprising a relatively thick ring shaped wall structure having a pair of outer substantially planar bearing surfaces and providing a relatively large opening defined by internal surfaces which intersect said bearing surfaces, at least one of said bearing surfaces serving to be engaged by a substantially planar surface of a complementary section whereby the latter in combination with said opening defines a chamber for receiving a sample of such a liquid, said wall structure being provided with an entrance through which the sample enters such a chamber, and said wall structure also being provided with an integral formation extending outwardly from said entrance for accommodating an inner extremity of a tubular means for receiving a sample for flow into such a chamber.

2. The section defined in claim 1, including a complementary section which engages one of said bearing surfaces to define a chamber.

3. The section defined in claim 1, including a pair of complementary sections each of which has a substantially planar surface and these surfaces respectively engage said bearing surfaces and in combination with said opening define a substantially closed chamber.

4. The section defined in claim 1, in which at least one of said bearing surfaces is provided with a groove affording a vent for such a chamber.

5. The section defined in claim 1, in which said integral formation is in the form of a channel, including a complementary section which has an enlarged portion which covers one end of said opening and a narrow portion which substantially covers said channel.

6. A section of a device for obtaining a sample of hot liquid, said section comprising wall structure having an upper outer surface and a lower outer surface which determine a substantially uniform cross dimension to this structure and surfaces which are disposed transverse to said outer surfaces and determine the thickness of said wall structure and provide an enlarged open ended enclosure, said wall structure being provided with an entrance communicatively connected with the interior of said enclosure, and at least one of said outer surfaces providing a bearing surface for a planar surface of a complementary section whereby this planar surface closes off one end of said enclosure and forms in combination therewith a chamber for receiving a sample of such a liquid for entry into the chamber through said entrance.

7. A section for use in a device for obtaining a sample of a hot liquid, said section comprising wall structure forming an enlargement having outer substantially planar parallel bearing surfaces and an enlarged opening extending transversely through this enlargement and intersecting said surfaces, at least one of said surfaces serving to be engaged by a complementary planar section for closing off one end of said opening to provide in combination therewith a primary chamber for receiving such a liquid, said wall structure also being provided with an entrance located between said outer surfaces and communicating with said chamber, and said wall structure also being provided with a laterally extending formation for accommodating a tubular means for receiving such a liquid for flow into said chamber via said entrance.

8. A subassembly of a device for obtaining a sample of hot liquid from a supply thereof, said subassembly comprising a center section of substantially uniform thickness having outer substantially planar bearing surfaces and a relatively large opening extending transversely therethrough, a pair of outer sections having substantially planar inner surfaces engaging said bearing surfaces whereby said sections are arranged in a superimposed relationship so that said inner surfaces of said outer sections in combination with said opening to provide an enclosed chamber for receiving a sample of such a liquid, and said center section being provided with an entrance through which such a liquid can flow into said chamber and with a channel formation for supporting a tubular means for receiving such a liquid for flow through said entrance.

9. The subassembly defined in claim 8, in which said outer sections are appreciably thinner in cross-section than the center section and have portions which engage portions of said channel formation and so that the open side of the latter is substantially closed.

10. A relatively thick elongated section for use in a device for obtaining a sample of molten material, said section comprising an enlarged extremity provided with a relatively large opening extending transversely therethrough and a reduced channel extremity having a depth which is somewhat less than the depth of said opening.

11. The section defined in claim 10, including a thin section engaging said thick section and defining in combination with said enlarged extremity and opening a chamber for receiving a sample of molten material and defining in combination with said channel extremity a tubular formation for accommodating tubular means for initially accommodating such a material for flow into said chamber.

12. The section defined in claim 10, in which said enlarged extremity has a rim provided with a groove for the purpose described.

13. A subassembly of a device for obtaining samples of a molten material comprising a pair of elongated thick sections, a center section and a pair of outer sections, each of said thick sections having a rear enlargement provided with a relatively large opening extending transversely therethrough and a front reduced formation, and means securing said sections in a superimposed relationship in which said center section is disposed between said thick sections and said outer sections respectively engage said thick sections to provide a pair of substantially closed chambers, said formations serving to respectively accommodate a pair of tubular means through which such a material may be caused to flow into said chambers for receiving samples of the material.

14. A subassembly of a device for obtaining a sample of a molten material comprising an elongated relatively thick center section having a rear enlargement provided with a large opening extending transversely therethrough and a reduced front formation, and a pair of relatively thin outer sections secured in relation to said enlargement so as to provide a chamber, and one of said outer sections forming in combination with said reduced formation a generally tubular formation for accommodating a tubular means for receiving some of such a material for flow into said chamber whereby to obtain a sample.

15. A subassembly for the purpose described comprising three mating sections, one of said sections being relatively thick and having an enlargement provided with a large opening extending transversely therethrough, the other of said sections being relatively thin and disposed in a juxtaposed relation to said enlargement and opening to provide a substantially closed chamber, and a reduced formation extending from enlargement for accommodating a tubular means through which a molten material may be caused to flow into said chamber for obtaining a sample of such a material.

16. An elongated section of a device for obtaining a sample of molten material from a supply thereof, said section having a relatively thick rear enlarged extremity provided with an opening and a front channel extremity which is relatively deep so that a pair of tubular means may be secured therein for receiving molten material for flow into said opening.

17. The section defined in claim 16, including a complementary thin section cooperating with said enlargement and opening therein to provide a substantially closed chamber for receiving such a material.

18. A subassembly of a device for obtaining a sample of a molten material from a supply thereof, said subassembly comprising a relatively thick section having a rear hollow enlargement and a front relatively deep channel portion extending therefrom, and a pair of elongated tubular means having inner extremities secured in said channel and outer extremities for receiving such a material for flow into said enlargement.

19. The subassembly defined in claim 18, including a relatively thin section having an enlargement disposed in a superimposed relation to the enlargement of said thick section to define in combination therewith a chamber for such a material, and also having an extension cooperable with said channel portion to provide a substantially tubular formation in which said inner extremities of said tubular means are confined.

20. A subassembly of a device for obtaining samples of a molten material comprising a pair of elongated thick sections, a center section and a pair of outer sections, each of said thick sections having a rear enlargement provided with a relatively large opening extending transversely therethrough and a front reduced channel, and means securing all of said sections in a superimposed relationship in which said center section is disposed between said thick sections and said outer sections respectively engage said thick sections to provide a pair of substantially closed chambers, said channels serving to respectively accommodate a pair of tubular means through which such a material may be caused to flow into said chambers for receiving samples of such a material.

21. A subassembly of a device for obtaining a sample of a molten material comprising an elongated relatively thick center section having a rear enlargement provided with a large opening extending transversely therethrough and a reduced front portion, and a pair of relatively thin outer sections secured in relation to said enlargement so as to provide a chamber, and one of said outer sections forming in combination with said reduced portion a generally tubular formation for accommodating a tubular means for receiving some of such a material for flow into said chamber whereby to obtain a sample.

22. A subassembly comprising three mating sections, one of said sections being relatively thick and having an enlargement provided with a large opening extending transversely therethrough, the other sections being relatively thin and disposed in a juxtaposed relation to said enlargement and opening to provide a substantially closed chamber, and a reduced channel extending from said enlargement for accommodating a tubular means through which a molten material may be caused to flow into said chamber for obtaining a sample.

23. A device for obtaining a sample of hot liquid from a supply thereof, said device comprising an elongated outer housing and an assembly secured in a front extremity thereof, said assembly comprising: a center section of substantially uniform thickness having outer substantially planar bearing surfaces and a relatively large opening extending transversely therethrough, a pair of outer sections having substantially planar inner surfaces engaging said bearing surfaces whereby said sections are arranged in a superimposed relationship so that said inner surfaces of said outer sections in combination with said opening provide an enclosed chamber for receiving a sample of such a liquid, said center section being provided with an entrance, and tubular means communicatively connected to said entrance through which such a liquid can flow into said chamber, and a rear extremity of said outer housing being constructed for detachable connection with a lance.

24. A device for obtaining a sample of molten material from a supply thereof comprising an elongated outer housing and an assembly secured in a front extremity thereof, said assembly comprising: a relatively thick elongated section having an enlarged rear extremity provided with a relatively large opening extending transversely therethrough and a front reduced channel extremity having a depth which is somewhat less than the depth of said opening, a thin section engaging said thick section and defining in combination with its rear extremity and opening a chamber for receiving a sample of molten material and defining in combination with said channel extremity a tubular formation, and tubular means secured in said tubular formation for initially receiving such a material for flow into said chamber.

25. A device for obtaining samples of molten material from a supply thereof comprising an outer elongated housing and an assembly secured in a front extremity thereof, said assembly comprising: a pair of elongated thick sections, a center section and a pair of outer sections, each of said thick sections having a rear enlargement provided with a relatively large opening extending transversely therethrough and a front reduced channel, means securing said sections in a superimposed relationship in which said center section is disposed between said thick sections and said outer sections respectively engage said thick sections to provide a pair of substantially closed chambers and a pair of tubular formations, and a pair of tubular means respectively secured in said formations through which such a material may be caused to flow into said chambers for receiving samples of the material.

26. A device for obtaining a sample of molten material from a supply thereof comprising an elongated outer housing and an assembly secured in a front extremity thereof, said assembly comprising an elongated relatively thick center section having a rear enlargement provided with a large opening extending transversely therethrough and a reduced front portion, a pair of relatively thin outer sections secured in relation to said enlargement and said front portion so as to provide a chamber and one of said outer sections forms in combination with said front portion a generally tubular formation, and tubular means secured in said tubular formation for receiving some of such a material for flow into said chamber whereby to obtain a sample.

27. Structure for the purpose described comprising three mating sections, one of said sections being relatively thick and having an enlargement provided with a large opening extending transversely therethrough, the other sections being relatively thin and disposed in a juxtaposed relation to said enlargement and opening to provide a substantially closed chamber, a reduced integral formation extending from said enlargement, tubular means disposed in said formation through which a molten material may be caused to flow into said chamber for obtaining a sample of such a material, means for holding the sections and tubular means assembled, and an elongated outer housing secured about said sections so that an outer end of said tubular means extends forwardly of said housing.

28. A device for obtaining samples of molten material from a supply thereof comprising an elongated outer housing and structure mounted in a front extremity thereof, said structure comprising a pair of elongated thick sections, a center section and a pair of outer sections, each of said thick sections having a rear enlargement provided with a relatively large opening extending transversely therethrough and a front reduced channel, means securing all of said sections in a superimposed relationship in which said center section is disposed between said thick sections and said outer sections respectively engage said thick sections to provide a pair of substantially closed chambers and a pair of tubular formations, and a pair of tubular means respectively secured in said formations through which such a material may be caused to flow into said chambers for receiving samples of such a material.

29. A device for obtaining a sample of molten material from a supply thereof comprising an elongated outer housing and structure mounted in a front extremity thereof, said structure comprising an elongated relatively thick center section having a rear enlargement provided with a large opening extending transversely therethrough and a reduced front channel portion, a pair of relatively thin outer sections secured in relation to said enlargement so as to provide a chamber and so that one of said outer sections in combination with said channel portion forms a generally tubular formation, and tubular means secured in said tubular formation for receiving some of such a material for flow into said chamber whereby to obtain a sample.

30. A device for obtaining a sample of molten material comprising an elongated outer housing and an assembly mounted in a front extremity thereof, said assembly comprising three mating sections, one of said sections being relatively thick and having an enlargement provided with a large opening extending transversely therethrough, the other sections being relatively thick and disposed in a juxtaposed relation to said enlargement and opening to provide a substantially closed chamber, a reduced integral channel extending from said enlargement and in combination with one of said other sections providing a tubular formation, and tubular means secured in said formation through which a molten material may be caused to flow into said chamber for obtaining a sample.

31. An elongated one-piece casing having a rear tubular extremity and an elongated forwardly extending bifurcation for accommodating between the furcations and in said rear extremity thereof a structure for receiving a sample of molten material from a supply thereof.

32. An elongated one-piece casing having a rear tubular extremity and an elongated forwardly extending bifurcation, structure disposed between the furcations of said bifurcation and in said rear extremity for receiving a sample of molten material from a supply thereof, and means for holding said furcations about such a structure.

33. An elongated casing constituting a component of a structure for obtaining a sample of molten material, said casing having a rear tubular extremity for accommodating a rear part of such a structure and a pair of forwardly extending relatively movable portions formed to provide a pair of opposed intermediate side openings for accommodating intermediate portions of such a structure and front channels for accommodating frontal portions of such a structure therebetween.

34. An elongated casing constituting a component of a structure for obtaining a sample of molten material, said casing having a rear tubular extremity and a pair of elongated forwardly extending relatively movable portions which are formed to provide a pair of opposed side openings for accommodating an intermediate portion of such a structure and front channels for accommodating a frontal portion of such a device.

35. A subassembly of a device for obtaining a sample of molten material from a supply thereof, said subassembly comprising an elongated casing having a rear tubular extremity and a pair of substantially corresponding forwardly extending relatively movable portions formed to provide a pair of intermediate side openings and a pair of front channels, elongated wall strucure forming an enlargement provided with a chamber, a rear opening and a front generally tubular formation, an outlet tube secured in said rear opening and projecting rearwardly from said enlargement, an entrance tube secured in said tubular formation for receiving a sample of such a material for flow into said outlet tube via said chamber, said outlet tube being disposed in said rear extremity, said enlargement being disposed in and between said side openings, said tubular formation and at least a portion of said entrance tube being disposed between said channels, and means securing said relatively movable portions about said enlargement, tubular formation and at least a portion of said entrance tube for holding said wall structure and said tubes assembled in said casing.

36. A subassembly of a device for obtaining a sample of molten material from a supply thereof, said subassembly comprising wall structure having an enlargement provided with a chamber and a front generally tubular formation, rear tubular means carried by said enlargement communicating with said chamber and extending rearwardly from said enlargement, an entrance tube secured in said tubular formation for receiving a sample of such a material for flow into said tubular means via said chamber, an elongated casing having: a rear tubular extremity receiving said tubular means, a pair of intermediate opposed openings in which at least portions of said enlargement are disposed, and a pair of front channels between which said tubular formation and at least a portion of said entrance tube is disposed.

37. A device for obtaining a sample of molten material from a supply thereof, said device comprising an outer elongated housing and an elongated casing secured in said housing having a rear tubular extremity and a pair of substantially corresponding forwardly extending relatively movable portions formed to provide a pair of intermediate side openings and a pair of front channels, elongated wall structure forming an enlargement provided with a chamber, a pair of rear openings and a front generally tubular formation, a pair of outlet tubes respectively secured in said rear openings and projecting rearwardly from said enlargement, an entrance tube secured in said tubular formation and having a front end extending forwardly of said housing for receiving a sample of such a material for flow into said outlet tube via said chamber, said outlet tube being disposed in said rear extremity, said enlargement being disposed in and between said side openings, said tubular formation and at least a portion of said entrance tube being disposed between said channels, and means securing said relatively movable portions about said enlargement, tubular formation and at least a portion of said entrance tube for holding said wall structure and tubes assembled in said casing.

38. A subassembly of a device for obtaining a sample of molten material from a supply thereof, said subassembly comprising wall structure having an enlargement provided with a chamber and a front generally tubular formation, an entrance tube secured in said tubular formation for receiving a sample of such a material for flow into said chamber, an elongated casing having a pair of intermediate opposed openings in which at least portions of said enlargement are disposed, and a pair of channels between which said tubular formation and at least a portion of said entrance tube is disposed.

* * * * *